United States Patent [19]

Rancke-Madsen et al.

[11] Patent Number: 6,087,148

[45] Date of Patent: Jul. 11, 2000

[54] METHOD OF PURIFICATION OF CELLULOSE FROM A BROTH SOLUTION BY CRYSTALLIZATION

[75] Inventors: Anders Rancke-Madsen, Charlottenlund; Mads Aage Laustsen, Lyngby, both of Denmark

[73] Assignee: Novo Nordisk A/S, Bagsvaerd, Denmark

[21] Appl. No.: 09/143,206

[22] Filed: Aug. 28, 1998

Related U.S. Application Data

[63] Continuation of application No. PCT/DK97/00113, Mar. 14, 1997.

[30] Foreign Application Priority Data

Mar. 15, 1996 [DK] Denmark .................................. 0305/96

[51] Int. Cl.[7] .............................. C12N 9/42; C30B 29/58
[52] U.S. Cl. ........................ 435/209; 435/816; 117/927
[58] Field of Search ................................... 435/183, 209, 435/816; 514/334, 412, 418; 117/11, 927

[56] References Cited

U.S. PATENT DOCUMENTS

| 3,664,926 | 5/1972 | Grabner et al. | 435/229 |
|---|---|---|---|
| 5,763,254 | 6/1998 | Woldike et al. | 435/209 |

FOREIGN PATENT DOCUMENTS

| WO 91/10677 | 7/1991 | WIPO . |
|---|---|---|
| 95/01989 | 1/1995 | WIPO . |
| WO 95/01989 | 1/1995 | WIPO . |
| 97/34919 | 9/1997 | WIPO . |

OTHER PUBLICATIONS

Joliff et al., J. Mol. biol., "Crystallization and Preliminary X–ray Diffraction Study of an Endoglucanase from Clostridium thermocellum", 189(1), p. 249–250, May 1986.
Joliff et al., Bio/Technology, "Isolation, Crystallization and Properties of a New Cellulase of Clostridium themocellum Overproduced in *Escherichia coli*", 4, pp. 896–900, Oct. 1986.
Davies et al., J. Mol. Biol., "Crystallization and Preliminary X–ray Analysis of a Fungal Endoglucanase I", 2228(3), pp. 970–972, Dec. 1992.
Spezio et al., Biochemistry, "Crystal Structure of the Catalytic Domain of a Thermophilic Endocellulase", 32(38), pp. 9906–9916, Sep. 1993.
Davies e al., Nature, "Structure and Function of Endoglucanse V", 365(6444), pp. 362–364, Sep. 1993.
Hata et al., J. Mol. Biol., "Crystallization and Preliminary X–ray Diffraction Studies of an Endoglucanase from *Aspergillus aculeatus*", 241 (2), pp. 278–280, Aug. 1994.
Chauvaux et al., J. Biol. Chem., "Structural and Functional Analysis of the Metal–Binding Sites of *Clostridium thermocellum* Endoglucanase CelD", 270(17), pp. 9757–9762, Apr. 1995.
Chitarra et al., J. Mol. Biol., "Multiple Crystal Forms of Endoglucanase CelD: Signal Peptide Residucs Modulate Lattice Formation", 218(2), pp. 225–232, Apr. 1995
Hahn et al., FEBS Letts., "Crystal Structure of *Bacillus licheniformis* 1,3–1,4–beta–D–Glucan 4–Glucanohydrolase at 1.8 Angstrom Resolution", 374(2), pp. 221–224, Aug. 1995.
Souchon et al., Prot. Struct. Funct. Genet., "Crystallization of a Family 8 Cellulase from *Clostridium thermocellum*", 25(1), pp. 134–136, May 1996.
Dounce et al. Prep. Biochem. (1981) 11(5): 501–523 (abstract only).
McPherson, A., Method in Enzomol. (1985) 114:112–120.
Scopes, R.K. "Protein Purification: Principles and Practice," 2nd edition, (1987) (Springer–Verlag: New York) p. 297–301.
Minoda et al. Agr. Biol. Chem. (1963) 27(11):806–11.
Kubo, Y. Toyama–ken Yakuji Kenkyusho Nenpo (1994) 21(21): 68–72 (abstract only).
McPherson, Eur. J. Biochem. (1990) "Protein Purification by Bulk Crystallization: The Recovery of Ovalbumin" 189:1–23.
Judge et al. (1995) Biotechnology and Bioengineering "Current Approaches To Macromolecular Crystallization" 48:316–323.

*Primary Examiner*—Jon P. Weber
*Attorney, Agent, or Firm*—Steve T. Zelson, Esq.; Reza Green, Esq.

[57] ABSTRACT

A method for purification, and isolation in crystalline form, of a cellulase from a broth comprises: treating the broth with a crystallization-effective amount of a water-miscible organic solvent (e.g. a lower aliphatic alcohol or ketone); and isolating the cellulase in question in crystalline form.

8 Claims, No Drawings

METHOD OF PURIFICATION OF CELLULOSE FROM A BROTH SOLUTION BY CRYSTALLIZATION

CROSS-REFERENCE TO RELATED APPLICATIONS

This application is a continuation of PCT/DK97/00113 filed Mar. 14, 1997 which claims priority under 35 U.S.C. 119 of Danish application 0305/96 filed Mar. 15, 1996, the contents of which are fully incorporated herein by reference.

FIELD OF THE INVENTION

The present invention relates to a simple, inexpensive and very effective method for crystallization of a protein, in particular an enzyme, present in a protein-containing solution, such as a fermentation broth.

BACKGROUND OF THE INVENTION

Enzymes for industrial purposes are usually provided as liquids or amorphous solids. Their availability as amorphous, rather than crystalline, solids is primarily due to the fact that the known methods for crystallization of enzymes are generally regarded as being too expensive to be used on an industrial scale.

There is an abundance of literature concerning crystallization of enzymes. It is difficult to generalize with respect to the outcome of specific crystallization procedures, as the art of enzyme crystallization is highly empirical.

Characteristic requirements of most of the hitherto known protein crystallization processes are: pure, concentrated initial solutions; very long crystallization times; and large amounts of chemicals, e.g. salts [see, e.g., *Biotechnology and Bioengineering* 48 (1995) pp. 316–323].

An industrial enzyme crystallization process which employs a water-soluble polymer (such as polyethylene glycol) has been described (see WO 95/01989).

SUMMARY OF THE INVENTION

It is an object of the present invention to provide an effective and inexpensive process by means of which a crystalline protein, in particular an enzyme, may be obtained from a solution containing the protein, and which does not require the addition of large amounts of chemicals such as salts. An important and very valuable feature of the process of the invention is that it permits the isolation of crystalline proteins, particularly enzymes, in a state of high purity, from an impure, protein-containing solution (i.e. a solution which, in addition to the protein in question, contains various other substances), especially a solution which contains other proteins, such as a solution derived from a fermentation broth.

The process of the invention makes it possible to obtain high yields using short crystallization times, and is simple, inexpensive, environmentally friendly, and compatible with industrial requirements.

Accordingly, the present invention provides a method for purification, and isolation in crystalline form, of a protein from a protein-containing solution, e.g. a solution which comprises more than one protein, such as a solution derived from a fermentation broth, the method comprising:

(a) treating the protein-containing solution with a crystallization-effective amount of a water-miscible (water-soluble) organic solvent; and (b) isolating the protein in question in crystalline form.

It will be understood that protein-containing solutions of particular relevance in the context of the invention are aqueous solutions (i.e., in general, solutions in which water constitutes substantially all of, or at least a major proportion of, the solvent liquid in which the protein of interest is dissolved).

DETAILED DISCLOSURE OF THE INVENTION

The present invention thus provides, inter alia, a method for crystallizing a protein (or a polypeptide) present in a fermentation broth. In this connection, the term "fermentation" is intended to refer not only to decomposition or transformation processes brought about by microorganisms (such as bacteria or fungi), but also to corresponding processes brought about by the agency of cells of animal or plant origin.

A fermentation broth will, besides the protein or polypeptide of interest, normally contain numerous other substances, such as substrate compounds, e.g. carbohydrates, salts, cells, and other metabolites (such as nucleic acids, and proteins or polypeptides other than the particular protein or polypeptide of interest).

When the method of the invention is to be applied to a fermentation broth, it is preferable that the broth is first subjected to one or more solid/liquid separatory techniques, e.g. flocculation, centrifugation, filtration or micro-filtration, or any combination thereof.

The method of the invention appears to work surprisingly well on relatively impure solutions, and it will normally not be necessary to purify a fermentation broth (or a protein-containing solution obtained by, e.g., solid/liquid separatory treatment of a fermentation broth) by means of chromatographic methods (for the purpose, for example, of removing extraneous proteins from the solution) before performing the method of the invention.

In another aspect of the invention, the protein-containing solution is concentrated before being treated with the organic solvent(s). Such concentration may suitably be achieved by one or more known procedures, e.g. by ultra-filtration (reverse osmosis) or by evaporation.

In a further aspect of the invention, the protein-containing solution may be subjected to a procedure for removal of low-molecular-weight substances (e.g. salts). Such treatments include diafiltration and dialysis.

Whilst concentration of the protein-containing solution is not essential for carrying out the method of the invention, it will often be desirable from the point of view of yield and ease of handling. Generally speaking, the concentration of the protein of interest in the protein-containing solution which is to be treated with organic solvent in accordance with the invention will be in the range of 0.1–25% by weight (% w/w; based on the weight of the protein-containing solution), preferably in the range of 0.5–15% w/w, in particular 5–15% w/w.

Preferred proteins in the context of the invention are—as already indicated to some extent above—enzymes, for example:

hydrolases (EC 3) [including proteases (peptidases, EC 3.4); carboxylic ester hydrolases (EC 3.1.1), such as lipases (e.g. triacylglycerol lipases, EC 3.1.1.3); glycosidases (EC 3.2), such as amylases (e.g. α-amylases, EC 3.2.1.1, β-amylases, EC 3.2.1.2, and glucoamylases, EC 3.2.1.3), cellulases (e.g. endo-1,4-β-glucanases, EC 3.2.1.4) and xylanases (e.g. xylan endo-1,3-β-xylosidases, EC 3.2.1.32)];

oxidoreductases (EC 1) [including phenol-oxidases such as laccases (EC 3.10.3.2) and other laccase-related enzymes classified under EC 1.10.3; and peroxidases (EC 1.11), such as those classfied under EC 1.11.1.7]; and isomerases (EC 5) [including xylose isomerases (EC 5.3.1.5)].

Enzymes

Enzyme classification numbers (EC numbers) referred to in the present specification with claims are in accordance with the *Recommendations* (1992) *of the Nomenclature Committee of the International Union of Biochemistry and Molecular Biology*, Academic Press Inc., 1992.

Proteases

Proteases (peptidases) which may be crystallized according to the present invention include proteases obtainable by fermentation processes employing cells, such as cells of a microorganism, especially a bacteria or a fungus. Chemically or genetically modified mutants of such proteases are included.

The protease may be a serine protease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in Wo 89/06270.

Suitable commercially available protease enzymes include those sold under the tradenames Alcalase, Savinase, Durazym, and Esperase by Novo Nordisk A/S (Denmark), those sold under the tradenames Maxatase, Maxacal, Maxapem and Properase by Gist-Brocades, those sold under the tradenames Purafect and Purafect OXP by Genencor International, and those sold under the tradenames Opticlean and Optimase by Solvay Enzymes.

Lipases

Lipases which may be crystallized according to the present invention include lipases obtainable by fermentation processes employing cells, such as cells of a microorganism, especially a bacteria or a fungus. Chemically or genetically modified mutants of such lipases are included Examples of appropriate lipases include a *Humicola lanuginosa* lipase, e.g. as described in EP 258 068 and EP 305 216, a *Rhizomucor miehei* lipase, e.g. as described in EP 238 023, a Candida lipase, such as a *C. antarctica* lipase, e.g. the *C. antarctica* lipase A or B described in EP 214 761, a Pseudomonas lipase, such as a *P. alcaligenes* or *P. pseudoalcaligenes* lipase, e.g. as described in EP 218 272, a *P. cepacia* lipase, e.g. as described in EP 331 376, a *P. stutzeri* lipase, e.g., as disclosed in GB 1,372,034, a *P. fluorescens* lipase, a Bacillus lipase, e.g. a *B. subtilis* lipase [Dartois et al., *Biochemica et Biophysica Acta* 1131 (1993), pp. 253–260], a *B. stearothermophilus* lipase (JP 64/744992) or a *B. pumilus* lipase (WO 91/16422).

Numerous cloned lipases may be of interest in the context of the invention. Cloned lipases include the *Penicillium camembertii* lipase described by Yamaguchi et al. [*Gene* 103 (1991), pp. 61–67], the *Geotricum candidum* lipase [Schimada et al., *J. Biochem*. 106 (1989), pp. 383–388], and various Rhizopus lipases such as an *R. delemar* lipase [Hass et al., *Gene* 109 (1991), pp. 117–113], an *R. niveus* lipase [Kugimiya et al., *Biosci. Biotech. Biochem*. 56 (1992), pp. 716–719] and an *R. oryzae* lipase.

Other types of lipolytic enzymes, such as cutinases, may also be crystallized according to the invention. Examples of relevant cutinases are cutinase derived from Pseudomonas *mendocina* (as described in WO 88/09367), and cutinase derived from *Fusarium solani pisi* (described, e.g., in WO 90/09446).

Especially interesting lipases are commercially available lipases such as M1 Lipase™, Lumafast™ and Lipomax™ (Gist-Brocades), Lipolase™ and Lipolase Ultra™ (Novo Nordisk A/S), and Lipase P "Amano" (Amano Pharmaceutical Co. Ltd.).

Amylases

Amylases (such as α- or β-amylases) which may be crystallized according to the present invention include amylases obtainable by fermentation processes employing cells, such as cells of a microorganism, especially a bacteria or a fungus. Chemically or genetically modified mutants of such amylases are included Relevant amylases include, for example, α-amylases obtained from Bacillus, in particular a special strain of *B. licheniformis*, described in more detail in British Patent No. 1,296,839. Particularly interesting amylases are commercially available amylases, some non-limiting examples of which are Termamyl™, Fungamyl™ and BAN™ (available from Novo Nordisk A/S), and Rapidase™ and Maxamyl p™ (available from Gist-Brocades).

Related enzymes of interest in the context of the invention include CGTases (cyclodextrin glucanotransferases, EC 2.4.1.19), obtainable from, e.g., bacteria of the genera Bacillus, Thermoanaerobactor or Thermoanaerobacterium.

Cellulases

In the present context, the term "cellulase" refers to an enzyme which catalyses the degradation of cellulose to glucose, cellobiose, cellotriose and other cello-oligosaccharides.

A particularly suitable type of cellulase in the context of the invention is an endo-1,4-β-glucanase (EC 3.2.1.4), preferably a recombinant endo-1,4-β-glucanase.

Cellulases appropriate for crystallization according to the invention include microbial cellulases, notably bacterial or fungal cellulases. Relevant examples of bacterial cellulases are cellulases derived from or producible by bacteria within one of the following genera: Pseudomonas, Bacillus, Cellulomonas, Clostridium, Microspora, Thermotoga and Caldocellum, as well as Actinomycets such as Streptomyces, Termomonospora and Acidothemus. Relevant bacterial species in this connection include *Pseudomonas cellulolyticus, Bacillus lautus, Cellulomonas fimi, Microspora bispora, Termomonospora fusca, Termomonospora cellulolyticum* and *Acidothemus cellulolyticus*.

Relevant fungal cellulases include acid cellulases derived from or producible by fungi within the genera Trichoderma, Myrothecium, Aspergillus, Phanaerochaete, Neurospora, Neocallimastix and Botrytis, in particular a fungus chosen among *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum* and *Botrytis cinerea*.

Other interesting fungal cellulases are neutral or alkaline cellulases derived from or producible by fungi within the genera Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium, such as a fungus chosen among *Humicola insolens, Fusarium oxysporum, Myceliopthora thermophila, Penicillium janthinellum* and Cephalosporium sp., preferably a fungus chosen among *Humicola insolens* DSM 1800, *Fusarium oxysporum* DSM 2672, *Myceliopthora thermophila* CBS 117.65, and Cephalosporium sp. RYM-202.

Further cellulases of interest are variants having, as a parent cellulase, a cellulase of fungal or bacterial origin, e.g. a cellulase derivable from a fungal strain within one of the genera Humicola, Trichoderma and Fusarium.

Oxidoreductases

Oxidoreductases appropriate for crystallization according to the present invention include peroxidases, and oxidases such as laccases.

Peroxidases

Particularly interesting enzymes exhibiting peroxidase activity are those classified under enzyme classification EC 1.11.1.7, as well as fragments of such enzymes exhibiting peroxidase activity.

Peroxidases appropriate for crystallization by the method of the invention are suitably peroxidases producible by microorganisms such as fungi or bacteria. Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* DSM 2672, *Humicola insolens, Trichoderma resii, Myrothecium verrucana* IFO 6113, *Verticillum alboatrum, Verticillum dahlie, Arthromyces ramosus* FERM P-7754, *Caldariomyces fumago, Ulocladium chartarum, Embellisia alli* or *Dreschlera halodes*.

Other preferred fungi include strains belonging to the sub-division Basidiomycotina, class Basidiomycetes, e.g. Coprinus, Phanerochaete, Coriolus or Trametes, in particular *Coprinus cinereus* f. microsporus IFO 8371, *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the sub-division Zygomycotina, class Mycoraceae, e.g. Rhizopus or Mucor, in particular *Mucor hiemalis*.

Some preferred bacteria include strains of the order Actinomycetales, e.g. *Streptomyces spheroides* ATTC 23965, *Streptomyces thermoviolaceus* IFO 12382 or *Streptoverticillum verticillium* ssp. verticillium.

Other preferred bacteria include *Bacillus pumilus* ATCC 12905, *Bacillus stearothermophilus, Rhodobacter sphaeroides, Rhodomonas palustri, Streptococcus lactis, Pseudomonas purrocinia* ATCC 15958 and *Pseudomonas fluorescens* NRRL B-11. Further preferred bacteria include strains belonging to Myxococcus, e.g. *M. virescens*.

Particularly interesting peroxidases in relation to the method of the invention are recombinantly produced peroxidases, e.g. a peroxidase derived from a Coprinus sp., in particular *C. macrorhizus* or *C. cinereus* as described in WO 92/16634, or a variant thereof, e.g. a variant as described in WO 94/12621.

Laccases and Laccase-related Enzymes

In the context of the present invention, laccases and laccase-related enzymes include the following: any laccase enzyme comprised by the enzyme classification EC 1.10.3.2; any catechol oxidase enzyme comprised by the enzyme classification EC 1.10.3.1; any bilirubin oxidase enzyme comprised by the enzyme classification EC 1.3.3.5; and any monophenol monooxygenase enzyme comprised by the enzyme classification EC 1.14.18.1.

Appropriate laccases are laccases of microbial origin, notably laccases derived from bacteria or fungi (including filamentous fungi and yeasts). Suitable examples include laccases derivable from strains of Aspergillus, Neurospora, e.g. *N. crassa*, Podospora, Botrytis, Collybia, Fomes, Lentinus, Pleurotus, Trametes, e.g. *T. villosa* and *T. versicolor*, Rhizoctonia, e.g. *R. solani*, Coprinus, e.g. *C. plicatilis* and *C. cinereus*, Psatyrella, Myceliophthora, e.g. *M. thermophila*, Schytalidium, Polyporus, e.g. *P. pinsitus*, Phlebia, e.g. *P. radita* (WO 92/01046), or Coriolus, e.g. *C. hirsutus* JP 2-238885, in particular laccases obtainable from Trametes, Myceliophthora, Schytalidium or Polyporus.

Organic solvents

Water-miscible organic solvents which are suitable for use in the method of the invention are generally speaking substances which, at standard atmospheric pressure, are liquids at a temperature of, or in the vicinity of, 25° C. (including temperatures up to about 30° C.). Water-soluble polymers, such as the water-soluble polymers disclosed in WO 95/01989 (some of which—such as polyethylene glycols at the lower end of the molecular weight range therefor—may be liquids under the above-mentioned temperature and pressure conditions) are not within the scope of water-miscible organic solvents in the context of the present invention.

Suitable water-miscible solvents in the context of the invention include various lower aliphatic alcohols, notably $C_1$–$C_3$ aliphatic alcohols, and lower aliphatic ketones, notably $C_3$–$C_5$ ketones.

Preferred water-miscible organic solvents are solvents which are miscible with water in all proportions. Lower aliphatic alcohols within this category include all of the $C_1$–$C_3$ aliphatic alcohols (i.e. methanol, ethanol, 1-propanol and 2-propanol) and the $C_4$ alcohol tert-butyl alcohol (2-methyl-2-propanol); methanol, ethanol and 2-propanol are particularly preferred. Likewise, a preferred $C_3$–$C_5$ ketone is acetone (2-propanone).

Other water-miscible, lower aliphatic alcohols such as 2-butanol and isobutyl alcohol (2-methyl-1-propanol), and water-miscible $C_3$–$C_5$ ketones such as methyl ethyl ketone (2-butanone) and diethyl ketone (3-pentanone) may be appropriate for use in certain embodiments of the method of the invention.

Further water-miscible organic solvents of interest in the context of the present invention include glycols, notably lower aliphatic glycols (diols), such as ethylene glycol (1,2-dihydroxyethane), 1,2-propylene glycol (1,2-dihydroxypropane) and 1,3-propylene glycol (1,3-dihydroxypropane; also known as trimethylene glycol).

Although the use of water-soluble polymers such as polyethylene glycols and polypropylene glycols for crystallization of industrial enzymes from protein-containing solutions containing various other substances/impurities (including other proteins) has been described (see WO 95/01989), the present inventors are unaware of any previous disclosure to indicate or imply that simple, water-miscible organic solvents, such as ethanol and the like, could successfully and reliably be applied to obtain crystalline proteins from impure solutions thereof, particularly from solutions containing other protein species (such as solutions derived from fermentation broths). Indeed, such solvents appear to have been rather generally regarded as having a deleterious (e.g. denaturing) effect on protein molecules, such as enzymes, in aqueous solution. Thus, for example, a review article by A. McPherson [*Eur. J. Biochem.* 189 (1990), pp. 1–23] teaches (see p. 5 therein), in connection with the crystallization of proteins and nucleic acids, that (emphasis added):

". . . common methods for the crystallization of conventional molecules such as evaporation or solvent, dramatic temperature variation, or addition of *strong organic solvents are unsuitable and destructive*. They must be supplanted with more gentle and restricted techniques."

The latter document reference further teaches (see p. 12 therein), in relation to earlier reports of the use of organic solvents as precipitants for proteins or nucleic acids, that (emphasis added):

"In general, the most common organic solvents utilized have been ethanol, acetone, butanols and a few other common laboratory reagents . . . It might be noted here that organic solvents have been of more general use for the crystallization of nucleic acids, particularly tRNA and the duplex oligonucleotides. There they have been the primary means for crystal growth. This in part stems from the greater tolerance of polynucleotides to organic solvents and their polyanionic surfaces which appear to be even more sensitive to dielectric effects than are proteins.

The only general rules are that organic solvents should be used at low temperature, at or below 0° C., and they should be added very slowly and with good mixing . . . "

The McPherson reference further teaches (see p. 19 therein), in connection with the promotion of crystal growth of proteins, that (emphasis added):

"Certainly one major means of promoting periodic bond formation is to ensure that the population of molecules to be crystallized is as homogeneous as possible . . . It means not only that contaminating proteins of unwanted species be eliminated, but that within a target population all individuals assume absolute physical and chemical conformity."

It was thus very surprising to discover that crystallization of a desired protein, in particular an enzyme, from an impure, protein-containing solution (such as a solution derived from a fermentation broth, containing more than one protein species) can be achieved using a simple, water-miscible organic solvent, e.g. ethanol, without a need in general, for example, to operate at low temperatures or to take any special measures in connection with the addition of organic solvent, as taught by McPherson (loc. cit).

The water-miscible solvent employed in the method of the invention will normally be added to the protein-containing solution in question in an amount such that the concentration of solvent in the resulting mixture is in the range of 1–50% by weight (% w/w), often 5–50% w/w, such as 10–50% w/w, e.g. 20–45% w/w. However, in certain cases, such as when crystallizing certain lipases (lipolytic enzymes) by the method of the invention, it may be necessary to employ a much higher percentage of the solvent, e.g. in an amount corresponding to about 90% w/w, or possibly even more, of the solvent/protein-containing solution mixture.

Addition, in accordance with the invention, of water-miscible organic solvent to the protein-containing solution may take place, for example, by: introducing the solvent gradually and essentially continuously; or adding the solvent in several portions of the same or different sizes; or adding all the solvent in one portion. The choice of the manner in which the solvent is added will be based, inter alia, on the solubility characteristics not only of the protein or polypeptide of interest, but also of the various substances/impurities other than the protein in question.

By way of example, a situation in which a lipase is to be crystallized from a very impure protein-containing solution (derived, e.g., from a fermentation broth containing many components) may be considered: As indicated to some extent above, the solubility of lipases in aqueous media containing a high proportion of, e.g., a lower alcohol such as ethanol is often much greater than that of many other types of enzymes, and crystallization of such a lipase will require a concentration of, e.g., ethanol which is so high that other components of the protein-containing solution will separate from solution (e.g. precipitate) before a solvent concentration which is sufficient to initiate crystallization of the lipase is attained. In such cases, it will be desirable, in order to avoid contamination of the solid, crystalline lipase with solid-phase impurities, to add the organic solvent in portions at intervals sufficient to allow separation, and subsequent removal (e.g. by filtration), of unwanted solid-phase impurities to take place. When such impurities have separated from solution and been removed, further organic solvent may be added to increase the concentration thereof to a level sufficient to initiate crystallization of the enzyme of interest.

If appropriate, more than one water-miscible organic solvent may suitably be employed in the method of the invention. Thus, for example, a crystallization-effective amount of a mixture of two or more water-miscible organic solvents in suitable proportions may be employed to bring about crystallization of the protein of interest. Alternatively, for example, appropriate amounts of different water-miscible organic solvents may be added stepwise to the protein-containing solution.

In some embodiments of the method of the invention, appropriate salts may, in addition to water-miscible organic solvent, be added to the protein-containing solution. These will suitably be salts which may be employed in their own right for crystallization of proteins, e.g. enzymes, and such salts include acetates, sulphates ($HSO_4^-/SO_4^{2-}$), carbonates ($HCO_3^-/CO_3^{2-}$) and phosphates ($H_2PO_4^{2-}/HPO_4^{2-}/PO_4^{3-}$), e.g. alkali metal (such as $Li^+$, $Na^+$ or $K^+$) salts, alkaline-earth metal (such as $Ca^{2+}$) salts, or $Mg^{2+}$ salts thereof.

When, in the context of the invention, such salts are added, together with a water-miscible organic solvent, to a protein-containing solution, the appropriate amount of such a salt to be added will depend, inter alia, on the amount of organic solvent which is added. Thus, for example, when performing an embodiment of the method of the invention wherein a solvent concentration (in the mixture of protein-containing solution and water-miscible organic solvent) in the upper end of the normal range (e.g. in the vicinity of 50% w/w), a salt of the type in question will typically be introduced so as to give a salt concentration of up to 0.5–1% w/w. However, if a lower concentration of organic solvent is to used, it may be appropriate to increase the concentration of the salt.

It will be apparent that water-miscible organic solvents of the preferred types will generally be recoverable (e.g. by distillation) from the liquor remaining after crystallization of the protein in question has been completed, and it will thus be feasible—and from an enviromental and economic viewpoint highly desirable—to recycle and re-use such organic solvents in connection with the method of the invention.

Adjustment of pH

The pH of the protein-containing solution to which the water-miscible organic solvent(s) is, or has been, added will normally be adjusted to a value which is optimal with respect to crystallization and, preferably, protein stability. The optimum value for a given protein (e.g. enzyme) will depend, inter alia, on the exact nature thereof, and may be determined, for example, by performing a trial, typically starting by performing the crystallization procedure at pH 10, then at pH 9, pH 8, pH 7. . . and so on down to pH 3. If it is found, e.g., that the optimum for a given enzyme is between pH 4 and pH 5, a trial within this pH range may then be made to more precisely establish the optimum pH value. The optimum pH value for most enzymes will normally lie in the range from pH 4 to pH 9.

In some cases it may be advantageous to adjust the pH to a value equal to, or in the vicinity of, the isoelectric point (pI) for the protein in question. Thus, in certain embodiments of the method of the invention, pH is adjusted to a value such that $(pI-1) \leq pH \leq (pI+1)$.

In other cases it may be advantageous to alter the pH gradually during the crystallization process (i.e. to employ a pH gradient), or alternatively to carry out stepwise changes in pH during the crystallization process.

Any suitable acid or base may be used to adjust pH. Acids employed may be inorganic or organic. Some examples are hydrochloric acid, sulfuric acid, nitrous acid, phosphoric acid, acetic acid, citric acid and formic acid. Preferred acids are phosphoric acid, formic acid, citric acid, and acetic acid. Preferred bases are sodium hydroxide, potassium hydroxide and ammonium hydroxide, in particular sodium hydroxide.

Crystallization

Using the method of the invention it will normally be possible to carry out crystallization to a satisfactory extent—without having to add any seed crystals to start the crystallization—within a crystallization period of less than 48 hours, frequently within a period of 36 hours or less, and often within a period of 24 hours or less. Depending upon the specific conditions applying, including the nature of the protein or polypeptide to be crystallized and the nature of the other substances (impurities) present in the protein-containing solution, crystallization may often be achieved to a satisfactory extent within a period of 12 hours or less, and in some cases even within a period of about 6 hours.

Temperature

When using the method of the invention, crystallisation of the protein (e.g. enzyme) of interest will normally take place very satisfactorily at a temperature above 0° C. In general, the temperature of the protein-containing solution from which the protein is crystallized will suitably be from 0° C. to 40° C., preferably from 0° C. to 30° C., more typically from 5° C. to 30° C, such as from about 7° C. to about 28° C.

If appropriate, a temperature gradient may be employed, for example starting at a relatively low temperature (such as a temperature in the range of from about 0° C. to about 7° C.) and then increasing the temperature gradually (or alternatively in steps) up to the final desired temperature over a suitable period of time (e.g. over a period of up to several hours). In numerous embodiments of the method of the invention, the final temperature when employing gradual or stepwise temperature increase will often be in the vicinity of 25° C. (e.g. from about 22° C. to about 28° C.).

Isolation after Crystallization

The method of the invention causes the protein, e.g. enzyme, to crystallize. Isolation of the crystalline protein may be accomplished by conventional methods, e.g. by centrifugation and/or filtration, optionally with drying of the isolated product.

If the isolated protein, particularly an enzyme, is subsequently to be granulated, it may be appropriate to carry out a standard granulation procedure directly, starting from the moist, undried product. Drying will then take place during the granulation procedure.

If crystalline products of very high purity are desired, the initial, crystalline product of the method of the invention (which will generally be of rather high purity) may be redissolved to a suitable concentration in an appropriate aqueous medium and recrystallized, e.g. by the method of the invention. Other methods for recrystallization of substantially pure proteins, such as enzymes, may, however be employed. Recrystallization may, of course, be repeated one or more times, as desired.

The final crystalline product may be distributed and/or used as such. If desired, the crystals may, e.g., be dissolved (by the producer or by a consumer) to a suitable concentration in an appropriate medium to give a liquid-phase product.

The present invention further relates to a crystalline protein product obtainable by, or obtained by, a method according to the invention.

The purification/crystallization method of the present invention is believed to be applicable not only to proteins or polypeptides, but also to various other types of substances, including oligopeptides and compounds containing oligopeptide sequences. Such substances include, e.g., certain peptide hormones.

The invention is further illustrated in the following examples, which are not intended to limit the scope of the invention in any way:

EXAMPLE 1

Crystallization of *Humicola insolens* Cellulase Using Ethanol

A *H. insolens* cellulase (endo-1,4-β-glucanase) was cloned in *Aspergillus oryzae*. The fermentation broth containing the enzyme in question and other fermentation by-products was subjected to drum-filtration and then ultrafiltration (using Dow DDS Gr61pp membranes; cut-off ca. 20 kD). The ultrafiltration concentrate was further subjected to diafiltration using 2 volumes of deionized water to remove low-molecular-weight substances (such as salts). The resulting solution contained 87 grams of cellulase per liter (constituting 51% w/w of the dry-matter content of the solution), and had a pH of 6.7 and a specific conductivity of 0.7 mS/cm. 45.9 g of absolute (99.9%) ethanol was added with stirring to 100 g of the cellulase solution. The temperature was maintained at 27° C. After 17 hours, the resulting crystals were harvested by centrifugation. The yield was 85.4%, based on a determination of cellulolytic activity of the crystalline product redissolved in 0.1% w/w aqueous NaCl solution (eight-fold volume thereof relative to the volume of the crystals).

For determination of cellulolytic activity (expressed, e.g., in so-called S-CEVU units), a measured aliquot of the latter enzyme solution (crystalline product redissolved in 0.1% w/w NaCl) is incubated with carboxymethylcellulose (CMC; enzyme substrate). The reaction conditions are as follows:

| | |
|---|---|
| temperature: | 40° C. (thermostatted) |
| pH: | 7.5 (0.1 M phosphate buffer containing 0.1% w/w PEG 6000) |
| substrate concentration: | 3.11% (in the pH 7.5 buffer) |
| enzyme concentration range: | 0.097–0.181 S-CEVU/ml |
| incubation time: | 30 minutes. |

Cellulolytic degradation of the substrate results in a decrease in viscosity which is measured using a vibration viscosimeter (Mivi 3000, Sofraser, France). The decrease in viscosity is proportional to the cellulolytic activity of the sample. The activity in S-CEVU (Stabilized Cellulase Viscosity Units) is determined relative to an appropriate Novo Nordisk A/S cellulolytic enzyme standard.

EXAMPLE 2 (comparative example)

Crystallization of *Humicola insolens* Cellulase Using PEG 300

39.6 g of polyethylene glycol 300 (PEG 300; from BASF) was added with stirring to 100 g of the same cellulase solution as used in Example 1. The temperature was maintained at 27° C.

After 20 hours, the resulting crystals were harvested by centrifugation. The yield was 83%, determined as described in Example 1.

It is apparent from the above examples that the use of ethanol results in a higher yield of crystalline product than when PEG 300 is employed.

EXAMPLE 3
Crystallization of *Humicola insolens* Cellulase Using 2-propanol or Acetone A batch of raw fermentation broth containing *H. insolens* cellulase (endo-1,4-β-glucanase) cloned in *Aspergillus oryzae* was diluted with an equal weight of water. After adjustment of the pH of the diluted broth to 9.5 by addition of 10% (w/w) aqueous sodium hydroxide solution, it was subjected to drum filtration and then to germ-filtration using Seitz EK1 filter pads.

The resulting filtrate was subjected to ultrafiltration (using Dow DDS Gr61pp membranes) to a dry-matter content of 22% w/w. The ultrafiltration concentrate was further subjected to diafiltration using 3 volumes of tap water, and then to a carbon treatment using 3% (w/w) of Picatif™ FGV 120 active carbon at pH 5.5 for 2 hours at 30° C. The carbon was then removed by filtration through Seitz K900 filter pads and Seitz EK1 filter pads. The resulting concentrate had a specific conductivity of 1.06 mS/cm.

An indication of the level of purity of a given concentrate (cellulase-containing solution) is provided by the magnitude of the ratio of the optical density (OD) of the concentrate at 440 nm to the weight (in grams) of active cellulase in one liter of the solution, i.e. $OD_{440\ nm}$/g active cellulase. The higher the value, the lower the purity. For the carbon-treated, filtered concentrate referred to above, the value of this ratio was 21.7, which may be compared with the values given below (vide infra), measured in the same manner, for solutions made up from crystallized cellulase prepared using 2-propanol and acetone, respectively, as the water-miscible organic solvent in the method according to the invention.

After adjusting the pH of the carbon-treated, filtered concentrate to 6.5, aliquots were withdrawn in order to examine the effectiveness of 2-propanol and acetone, respectively, with respect to crystallization of the cellulase of interest.

Amounts of 30% w/w and 35% w/w (relative to the weight of the aliquot of concentrate), respectively, of each of the two solvents were added to, and mixed with, respective aliquots of concentrate at a temperature of about 5° C. After 15 minutes at this temperature, the temperature was raised to 28° C. and maintained at that temperature for 24 hours. The resulting crystal suspensions were harvested by centrifugation, and each of the crystal cakes were formulated by dissolution in an 8-fold volume of 0.1% (w/w) aqueous sodium chloride solution. The cellulase activity (in S-CEVU; see Example 1) and $OD_{440\ nm}$ were measured for each solution. The results are summarized in the table below:

| Amount of solvent | Yield of active cellulase in formulated product | | $OD_{440\ nm}$/(g active cellulase/1) in formulated product | |
|---|---|---|---|---|
| (% w/w) | 2-propanol | acetone | 2-propanol | acetone |
| 30 | 69% | 70% | 7.7 | 11.1 |
| 35 | 73% | 76% | 9.9 | 11.4 |

It is apparent from the above results that high yields and high purities of crystalline enzyme product (in this case a cellulase) are obtainable using 2-propanol or acetone as water-miscible organic solvent in embodiments of the method of the present invention.

What is claimed is:

1. A method for purification of a cellulase from a cellulase-containing fermentation broth, the method comprising:

(a) subjecting said broth to a solid/liquid separation procedure and a concentration procedure;

(b) contacting said separated and concentrated broth with a crystallization-effective amount of a $C_1$–$C_3$ aliphatic alcohol or a $C_3$–$C_5$ ketone; and (c) recovering the cellulase in crystalline form.

2. The method according to claim 1, wherein the concentration of said cellulase in said broth, prior to addition of said alcohol or ketone, is in the range of 0.1–25% w/w.

3. The method according to claim 1, wherein said crystallization takes place at a temperature above 0° C.

4. The method according to claim 1, wherein said alcohol or ketone is added to the broth at a concentration of between 1–90% w/w.

5. The method according to claim 4, wherein said alcohol or ketone concentration is between 5–50% w/w.

6. The method according to claim 5, wherein said alcohol or ketone concentration is between 20–45% w/w.

7. The method according to claim 1, further comprising, prior to step (a), adding a salt to the broth.

8. The method according to claim 1, further comprising, before or during steps (a) and/or (b), adjusting the pH of the broth.

* * * * *